(12) United States Patent
Li et al.

(10) Patent No.: US 6,558,943 B1
(45) Date of Patent: May 6, 2003

(54) METHOD FOR PROPAGATING FUNGI USING SOLID STATE FERMENTATION

(75) Inventors: Pei-Jung Li, Miaoli Hsien (TW); Chung-Guang Shen, Taipei (TW)

(73) Assignee: Sun Ten Pharmaceutical Co., Ltd., Taipei (TW)

( * ) Notice: Subject to any disclaimer, the term of this patent is extended or adjusted under 35 U.S.C. 154(b) by 2 days.

(21) Appl. No.: 09/655,435

(22) Filed: Sep. 5, 2000

(51) Int. Cl.$^7$ .................. C12N 1/18; A01N 63/04; A61K 31/56
(52) U.S. Cl. .............. 435/254.1; 424/93.5; 435/256.8; 514/169
(58) Field of Search .................. 435/254.1, 256.8, 435/174, 177, 424, 93.5, 514, 169

(56) References Cited

U.S. PATENT DOCUMENTS

| | | | |
|---|---|---|---|
| 3,884,759 A | 5/1975 | Nakao et al. ............... 435/52 |
| 4,472,907 A | 9/1984 | Wada et al. ............... 47/1.1 |
| 4,564,594 A | 1/1986 | Goldberg et al. .......... 435/139 |
| 4,877,731 A | 10/1989 | Ling et al. ................ 435/142 |
| 5,198,362 A | 3/1993 | Forsyth et al. ............. 435/254 |
| 5,582,828 A | 12/1996 | Lin et al. ................ 424/195.1 |
| 5,654,459 A | * 8/1997 | Balaraman et al. ......... 435/71.3 |
| 5,766,583 A | * 6/1998 | Luth et al. ................ 424/93.5 |
| 5,832,659 A | 11/1998 | Loftus et al. ............... 47/1.1 |
| 6,007,813 A | * 12/1999 | Taketomo et al. .......... 424/115 |
| 6,171,831 B1 | * 1/2001 | Tsai et al. ................. 435/142 |

FOREIGN PATENT DOCUMENTS

| | | |
|---|---|---|
| EP | CN 1 079 990 A | 12/1993 |
| EP | CN 1 208 575 A | 2/1999 |
| EP | CN 1 243 678 A | 2/2000 |
| JP | 07 227294 A | 8/1995 |
| WO | WO 99 21961 A | 5/1999 |

OTHER PUBLICATIONS

Durand A.; Solid State Fermentation; Biofutur. Le Mensuel Europeen De Biotechnology, Editioins Scientifiques Elsevier, Paris, Fr, 1998, vol. 181, p 41–43.

Barrios–Gonzalez J. et al.; Production of Secondary Metabolites by Solid–State Fermentation; Biotechnology Annual Review; 1996, vol. 2, p 85–121.

Zhu J–S. et al.; The Scientific Rediscovery of an Ancient Chinese Herbal Medicine: *Cordyceps sinensis*, Part I; The Journal of Alternative and Complementary Medicine; 1998, vol. 4, No. 3, p 289–303.

Riley, Ronald T., Plattner Ronald D.; Fermentation, Partial Purification, and Use of Serine Palmitoyltransferase Inhibitors from Isaria; Methods in Enzymology, 1999, Vol. 311, p 348–361.

* cited by examiner

Primary Examiner—David M. Naff
(74) Attorney, Agent, or Firm—Fei-Fei Chao; Venable, Baetjer, Howard & Civiletti

(57) ABSTRACT

A solid state fermentation (SSF) method is provided which is effective for both small- and large-scale fungal cultivation. Also provided is SSF media for fungal cultivation. The media preferably contains a carbon source and nitrogen source to provide a carbon to nitrogen ratio of about 5:1 to about 25:1 by weight. The media may also contain a vitamin and an inorganic substance. A preferred SSF medium contains malt extract, yeast extract, peptone, glucose, water, solid base, and calcium carbonate or gypsum. Before propagating fungal mycelia in the SSF medium, the mycelia may be pre-cultivated in a solid culture medium and then in a liquid medium. Although the SSF method can be used in growing most fungi, preferred fungi include *Cordyceps sinensis, Ganoderma lucidum, Antrodia camphorata, Trametes versicolor*, and *Agaricus blazei*. The SSF method not only produces high yield of fungi, but also stimulates the production of fungal metabolites, particularly the kinds with pharmaceutical and medicinal activities. *Cordyceps sinensis* is preferably grown to produce the active compound H1A which is a derivative of ergosterol.

30 Claims, 8 Drawing Sheets

METHOD FOR PROPAGATING FUNGI USING SOLID STATE FERMENTATION

I. FIELD OF THE INVENTION

Figure 1:
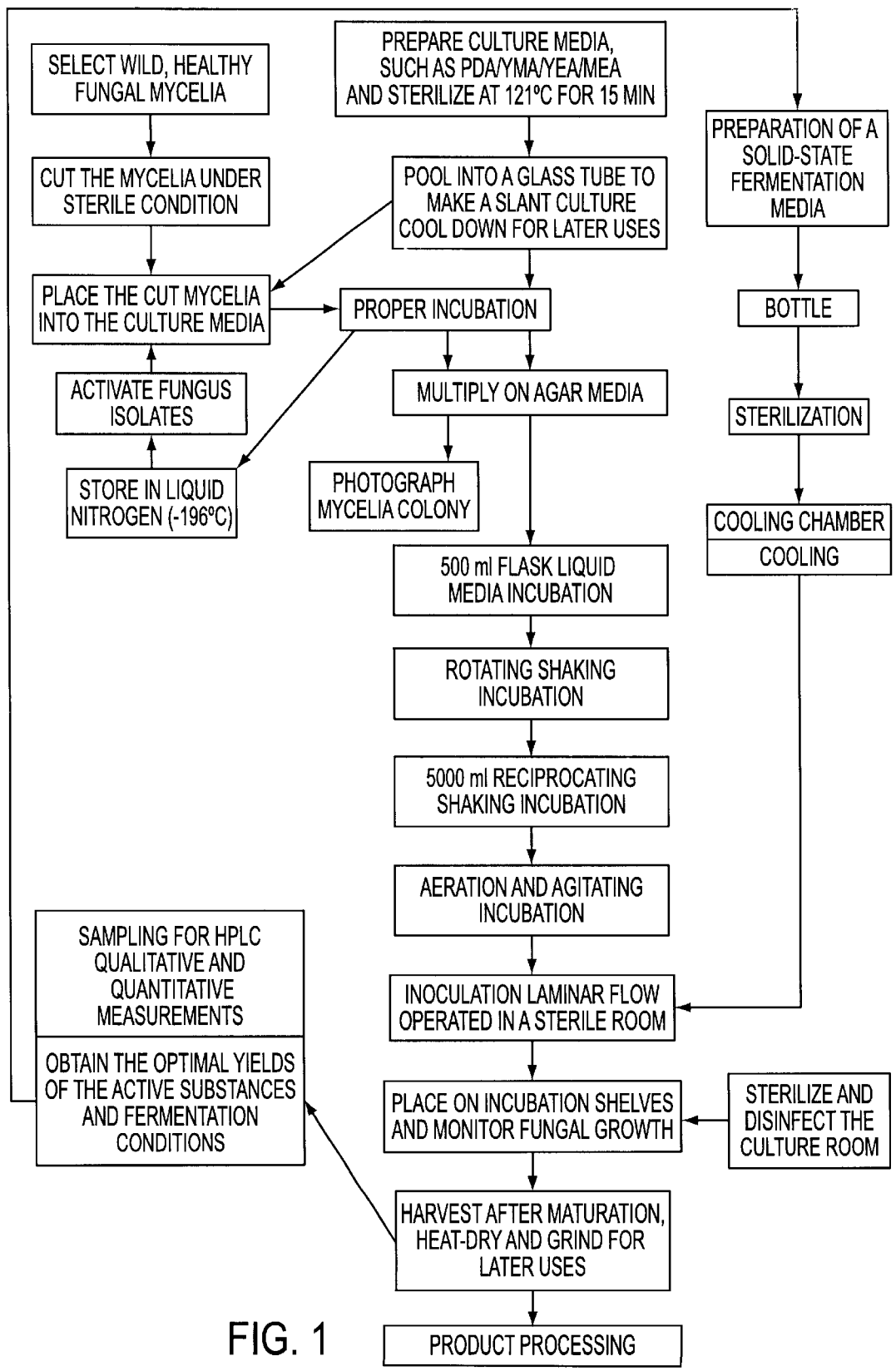

The present invention relates to a method for propagating fungi using solid state fermentation (SSF). SSF is particularly suitable for propagating fungi which are used for food, medicine, or health purposes. The kinds of fungi which can be propagated by SSF include, but not limited to, *Cordyceps sinensis, Trametes versicolor, Antrodia camphorata, Agaricus Blazei,* and *Ganoderma Lucidum*. The present invention also relates to the formulations and preparations of SSF media.

II. DESCRIPTION OF THE RELATED ART

*Cordyceps sinensis* is a parasitic fungus that has been used as a traditional Chinese medicine since ancient times. It is particularly famous for treating patients with kidney failure and asthma. It is also known for its anti-tumor effects.

Recently, Lin et al., *J. Lab. Clin. Med.*, 133:55–63 (1999), reported a finding of an active compound named "H1A" in the fruiting body of *Cordyceps sinensis*. H1A is a derivative of ergosterol having the chemical formula of:

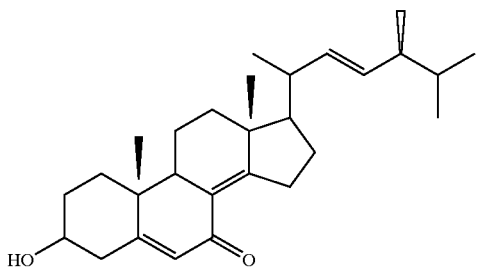

Ergosterol is (3β, 22E)-Ergosta-5,7,22-trien-3-ol. H1A appears to have pharmacological effects on the immune system, renal function, and cardiovascular system. It has also been known to have clinical effects on suppressing the activated human mesangial cells (HMC) and alleviating IgA nephropathy (Berger's Disease), thus, preventing the disease from progressing to the uremia stage. Lin et al.'s *J. Lab. Clin. Med.*, 133:55–63 (1999) article is herein incorporated by reference.

The authors of the *J. Lab. Clin. Med.*, 133:55–63 (1999) article, Lin et al., have a U.S. patent (U.S. Pat. No. 5,582,828) disclosing a method for identifying and isolating H1A from *Cordyceps sinensis*, which is also herein incorporated by reference.

Wild *Cordyceps sinensis* is extremely rare and difficult to obtain. The conventional cultivation methods for *Cordyceps sinensis* include solid media stationary incubation, liquid media rotating shaking incubation, liquid-state fermentation, and submerged liquid-state fermentation. Solid media stationary incubation uses solid media, such as malt extract agar (MEA), potato dextrose agar (PDA), or YEA (yeast extract agar), as culture media. Liquid media rotating shaking incubation and liquid-state fermentation use liquid media, such as malt extract broth (MEB), potato dextrose broth (PDB), or YEB (yeast extract broth) as culture media. They are known to be expensive and produce low yields of microorganisms. Moreover, it is not known that *Cordyceps sinensis* produced by these methods can generate a sufficient amount of H1A.

Submerged liquid-state fermentation is known for its capability of generating a high yield of microorganisms. However, this method requires high capital investment due to high energy and waste output. Also, because the fermentation cycle of the submerged liquid-state fermentation is generally short, usually five to seven days, it is doubtful that the metabolites generated by this method are sufficient enough to be of significance for medicinal uses.

Solid state fermentation (SSF) has been known for the production of enzymes and organic acids used in the paper pulp bleaching treatment industry and for producing organic pesticides. It is also widely used for producing soy sauce, alcoholic beverages from fruit or unpolished rice, and Chinese sour cabbage. SSF refers to the growth of microorganisms on moist solid substrates in systems with a continuous gas flow without the presence of free liquid between substrate particles. SSF has never been used for fungal propagation, particularly for fungi belonging to the classes of Ascomycotina and Basidomycotina in Eumycota.

There are two common types of solid bases used in an SSF culture. The first type uses "natural solid materials" as a solid base. For example, food stuffs or agricultural byproducts are used as a solid base not only to provide a physical matrix for microbial growth but also to be used as the main source of microbial nutrients. The second type uses an "inert solid support supplemented with nutrients" as a solid base. This type of solid base acts only as a physical support for microbial growth.

An SSF culture contains three phases, which are: (a) a solid phase which comprises the solid base as described above; (b) a liquid phase which is bound to the solid phase where intraparticle mass transfer occurs; and (c) a continuous gas phase. The gas phase controls the temperature and moisture of the SSF culture. It also provides oxygen for fungal growth.

In contrast to other fermentation methods, SSF requires low capital investment due to low energy and waste output. The base materials and media used in SSF are generally cheaper and simpler than other methods. In addition, the SSF medium generally contains low water content which not only reduces the risk of contamination but also offers a favorable condition for fungal growth, because it resembles the natural habitats for fungi. In fact, the SSF culture allows the fungal spores to proliferate because they can lay onto the surface of the solid base.

SSF is also known to have the following disadvantages. First, it is very difficult to monitor and control the parameters (such as moisture, pH, temperature, substrate concentration etc.) of the fermentation process in an SSF culture. Second, thus far the underlying scientific and engineering basis of SSF is still poorly understood. Finally, direct quantitative measurements for biomass in an SSF culture are difficult. In fact, many of the studies done so far on SSF have been done in either qualitative or empirical levels.

In the invention to be presented in the following sections, a method for propagating fungi using SSF will be described. The present invention not only will teach a useful SSF medium to grow fungi with high yields of metabolites but also will teach ways to monitor and control the parameters of the fermentation such as moisture, pH, temperature, and substrate concentration to maximize the production of fungi. The present invention also will provide direct quantitative and qualitative measurements of the biomass and active ingredients. Finally, the present invention will provide a method for effective production of *Cordyceps Sinensis* and its active substance H1A.

III. SUMMARY OF THE INVENTION

The present invention provides a method for propagating fungi, especially the kinds of fungi which can be used for food, medicine, and health purposes. The method applies solid state fermentation (SSF) to propagate fungi. The preferred kinds of fungi that can be used in SSF include, but are not limited to, *Cordyceps sinensis, Trametes versicolor, Antrodia camphorata, Agaricus blazei,* and *Ganoderma lucidum,* which are all within the classes of Ascomycotina and Basidomycotina. Among these fungi, *Cordyceps sinensis* is the most preferred kind.

It is preferred that before SSF is to be applied to the propagation of a fungus, certain pre-cultivation steps are to be followed. First, wild, healthy fungus isolates of proper quality are selected. Alternatively, fungus isolates stored in liquid nitrogen are activated. These fungus isolates are disinfected. Their mycelia are cut into pieces under sterile condition and placed into a solid culture medium in a glass tube or plate. The solid culture medium is made of appropriate culture media such as potato dextrose agar (PDA), yeast extract agar (YEA), malt extract agar (MEA), yeast malt agar (YMA), and peptone yeast glucose agar (PYG).

After the mycelia have multiplied to cover most of the medium, approximately 0.5 cm in diameter of the mycelia are cut and transferred toga flask containing a liquid culture medium. The liquid culture medium is made of appropriate culture media such as potato dextrose broth (PDB), yeast extract broth (YEB), malt extract broth (MEB), yeast malt broth (YMB), and peptone yeast glucose broth (PYGB). The mycelia are grown under rotating shaking conditions for about 8 days, preferably about 5–6 days. Then, the mycelia are transferred to a larger shaker flask containing the same or different liquid culture medium and incubated under reciprocating shaking conditions for no more than 6 days, preferably about 3–4 days. This is followed by aeration/agitation and further incubation for 4–5 days. At this stage, the cultivated mycelia are ready for the SSF.

The SSF medium suitable for fungi propagation comprises a carbon source, a nitrogen source, vitamins, and inorganic substances. Additionally, trace elements and organic substances can be added. The carbon source is derived from at least one of the following: starch, glucose, monosaccharide, polysaccharide, dextrin, maltose, saccharose, methyl cellulose, fructose, turanose, and corn powder. The nitrogen source is derived from at least one of the following: defatted soybean powder, peptone, yeast paste, yeast syrup, peanut cake powder, yeast powder, wheat bran, casein, calcium caseinate, and defatted beancake powder. Vitamins include, but are not limited to, vitamin $B_1$, vitamin $B_6$, and nicotinic acid. Inorganic substances include, but are not limited to, calcium sulfate and calcium carbonate. The preferred ratio of the carbon source (C) and the nitrogen source (N) is about 5:1 to 25:1 by weight.

During the SSF, pH, water content in the SSF medium, temperature, relative humidity, and light cycle are properly controlled. The pH is preferred to be controlled at pH 4.5 to 7. The temperature is preferred to be controlled at 22±50° C. The water content in the SSF medium is preferred to be between 40 and 70%. The relative humidity is preferred to be between 60 and 80%. The light cycle is preferred to be at 30% light and 70% dark.

Figure 2A:
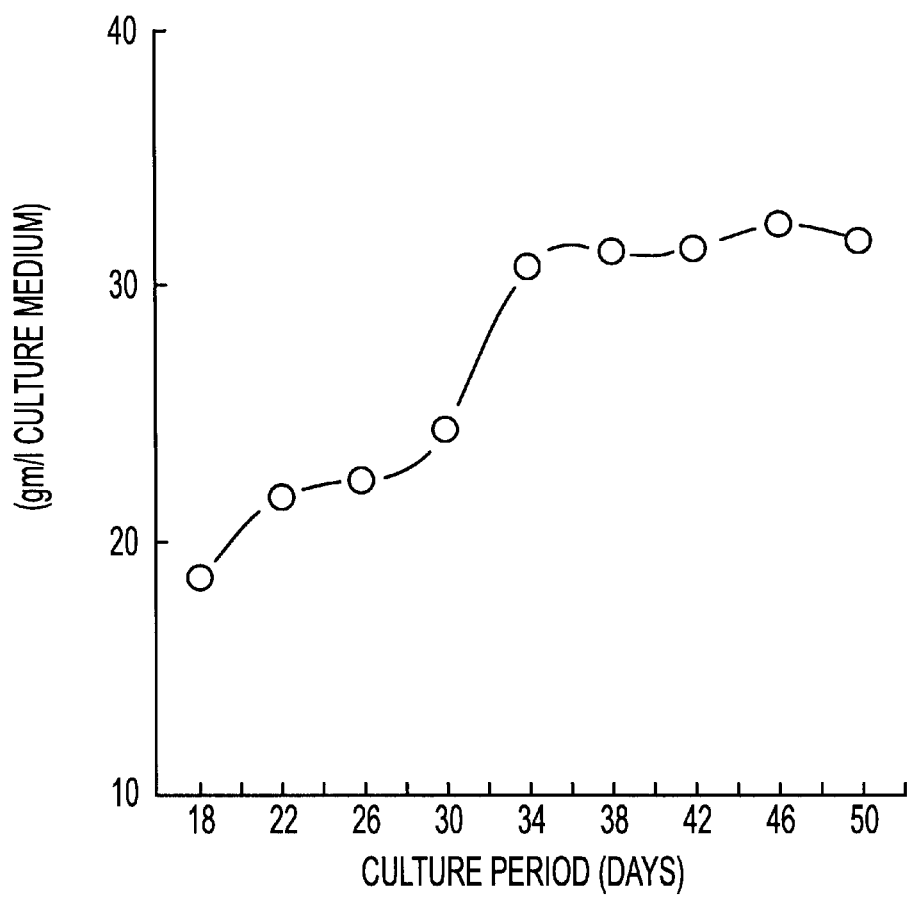
Figure 2B:
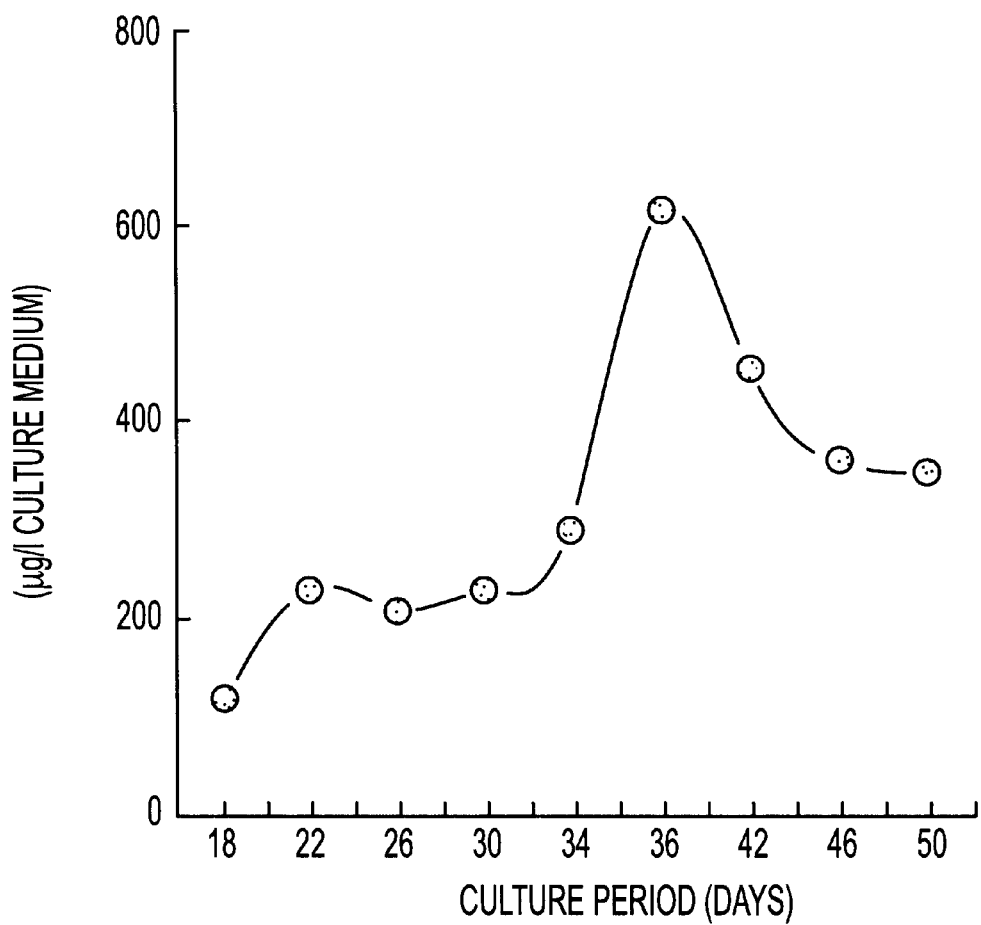

The incubation period for fungus in the SSF culture is normally between 20 and 60 days, preferably between 30 and 50 days. The longer the incubation period, the greater the production of the mycelium dry weight. However, prolonged incubation of fungus in the SSF culture does not guarantee that the production of active material/metabolite is also proportionally increased. For instance, as shown in FIG. 2a (infra), when *Cordyceps sinensis* is incubated in the SSF culture, the mycelial dried weight (g) increases during the first 34 days of incubation and plateaued between 34 and 50 days. On the contrary, as shown in FIG. 2b (infra), the amount of H1A, which is a derivative of ergosterol, is peaked at 38 days after incubation in the SSF culture. The amount of H1A decreases significantly during prolonged SSF incubation.

Due to this discrepancy, high performance liquid chromatography (HPLC) analysis of the total nucleoside amount and the amount of H1A/ergosterol is used in addition to the measurements of dried mass to determine when would be the proper time to harvest the fungi. The total nucleoside content not only reflects the active life cycles of the fungus (i.e., the higher the nucleoside content, the greater the replication of the fungus) but also may relate to pharmacological activities (i.e., the amount of adenosine in *Cordyceps sinensis* has been postulated by Dr. Ming-Shi Shiao of the Veteran Hospital in Taipei, Taiwan, to be related to its pharmacological activities). For purposes of producing higher quantity of active metabolites, such as H1A/ergosterol from *Cordyceps sinensis*, the amount of H1A/ergosterol is monitored and analyzed by HPLC.

Alternatively, the mycelia of the fungus grown in SSF for about 6 to 14 days can be transferred to another SSF for continuous cultivation of the fungus. In other words, the propagation of fungus in SSF can be continued for many generations as long as fresh SSF is provided.

As a specific example, the present invention also provides a method for propagating *Cordyceps sinensis* in an SSF culture using an SSF medium. As described above, the SSF culture is preferred to be preceded by pre-cultivation of the mycelia first in a slant culture medium comprising a solid medium such as PDA, YEA, MEA, YMA, and PGY followed by incubation of the mycelia in a liquid culture containing a liquid culture media such as PDB, YEB, MEB, YMB and PYGB.

The SSF medium contains malt extract, yeast extract, peptone, glucose, water, a solid base, and calcium carbonate/gypsum. Examples of a solid base include, but not limited to, rice, coarse rice/unpolished rice, corn, wheat, nude wheat, oat, and oatmeal. It is preferable that the SSF medium contains 0.3–4% by weight of malt extract, 0.3–4% by weight of yeast extract, 0.1–2% by weight of peptone, 1–5% by weight of glucose, 30–70% by weight of water, 40–60% by weight of solid base, and 2% by weight of calcium carbonate or gypsum.

The SSF medium is made by first mixing malt extract, yeast extract, peptone, glucose, water, and a solid base together and heating them to boiling to form a solid base mixture. Then, the solid base mixture is allowed to cool down. Finally, calcium carbonate or gypsum is added to the cooled solid base mixture and the final mixture is granulated. The SSF granules are placed into a SSF bottle and sterilized. After the mycelia have been inoculated, aerated, and thoroughly mixed with the SSF granules, the SSF granules-containing bottle is sat on the shelf in the incubator until harvest time.

The SSF incubation period for *Cordyceps sinensis* is determined either by the total nucleoside content or the amount of H1A and/or ergosterol in the dried mycelium of *Cordyceps sinensis*, both monitored and quantified by BPLC. The mycelia of *Cordyceps sinensis* in SSF can be transferred to a fresh SSF so that the propagation of *Cordyceps sinensis* can be continued.

The present invention further provides two SSF media. The first SSF comprises a carbon source, a nitrogen source, vitamin, and inorganic substance. The carbon source comprises at least one of the following: starch, glucose, monosaccharide, polysaccharide, dextrin, maltose, saccharose, methyl cellulose, fructose, turanose, and corn powder. The nitrogen source comprises at least one of the following: defatted soybean powder, peptone, yeast paste, yeast syrup, peanut cake powder, yeast powder, wheat bran, casein, calcium caseinate, and defatted beancake powder. The vitamin comprises at least one of the following: vitamin $B_1$, vitamin $B_6$, and nicotinic acid. The inorganic substance comprises at least one of the following: calcium sulfate and calcium carbonate. The preferred carbon source (C) and nitrogen source (N) ratio is 5:1 to 25:1 by weight.

The second SSF medium comprises 0.3–4% by weight of malt extract (preferably 0.5–3%, and most favorably 2%), 0.3–4% by weight of yeast extract (preferably 0.5–3%, and most favorably 2%), 0.1–2% by weight of peptone (preferably 0.3–1%, and most favorably 0.5%), 1–5% by weight of glucose (preferably 2–4%, and most favorably 2%), 30–70% by weight of water (preferably 40–60%, and most favorably 50%), 30–70% by weight of solid base (preferably 40–60%, and most favorably 50%), and 0.3–4% by weight of calcium carbonate or gypsum (preferably 0.5–3%, and most favorably 2%).

IV. BRIEF DESCRIPTION OF THE DRAWING

FIG. 1 is a flow-chart which shows stepwise preparation of fungal culture media and propagation of fungus. The left column shows how wild, healthy or frozen fungus mycelia are chosen. The central column contains three incubation steps, which are (1) a solid culture (such as a slant culture), (2) a liquid culture, and (3) a solid state fermentation (SFF) culture. The right column shows how a SFF culture is prepared.

FIG. 2 is a time course (days) of *Cordyceps Sinensis* in an SSF culture which shows the correlation between the total dried weight (gm) of *Cordyceps Sinensis* and the days of incubation in the SSF medium (FIG. 2a) and the correlation between the amount ($\mu$g) of H1A in *Cordyceps Sinensis* and the days of incubation in the SSF medium (FIG. 2b).

FIG. 3 shows the detection of H1A by reverse phase high performance liquid chromatography (RP-HPLC) at 280 nm. FIG. 3a is a RP-HPLC chromatogram showing the retention time for H1A. Purified H1A was a gift from Dr. Ching-Yuang Lin of U.S. Pat. No. 5,582,828. The chromatogram indicates that H1A could be further subdivided into 4 compounds (i.e., H1A-1, H1A-2, H1A-3, and H1A-4) with retention time spanned between 32 and 54 minutes (H1A-1:32.5 minutes; H1A-2:52.5 minutes; H1A-3:53.5 minutes; H1A-4:34 minutes). FIGS. 3b–e show the spectrum of H1A-1 (FIG. 3b ), H1A-2 (FIG. 3c ), H1A-3 (FIG. 3d), and H1A-4 (FIG. 3e). Only H1A-1 and H1A-3 show an absorbance peak at 277.7 nm and 274.1 nm, respectively.

Figure 4A:
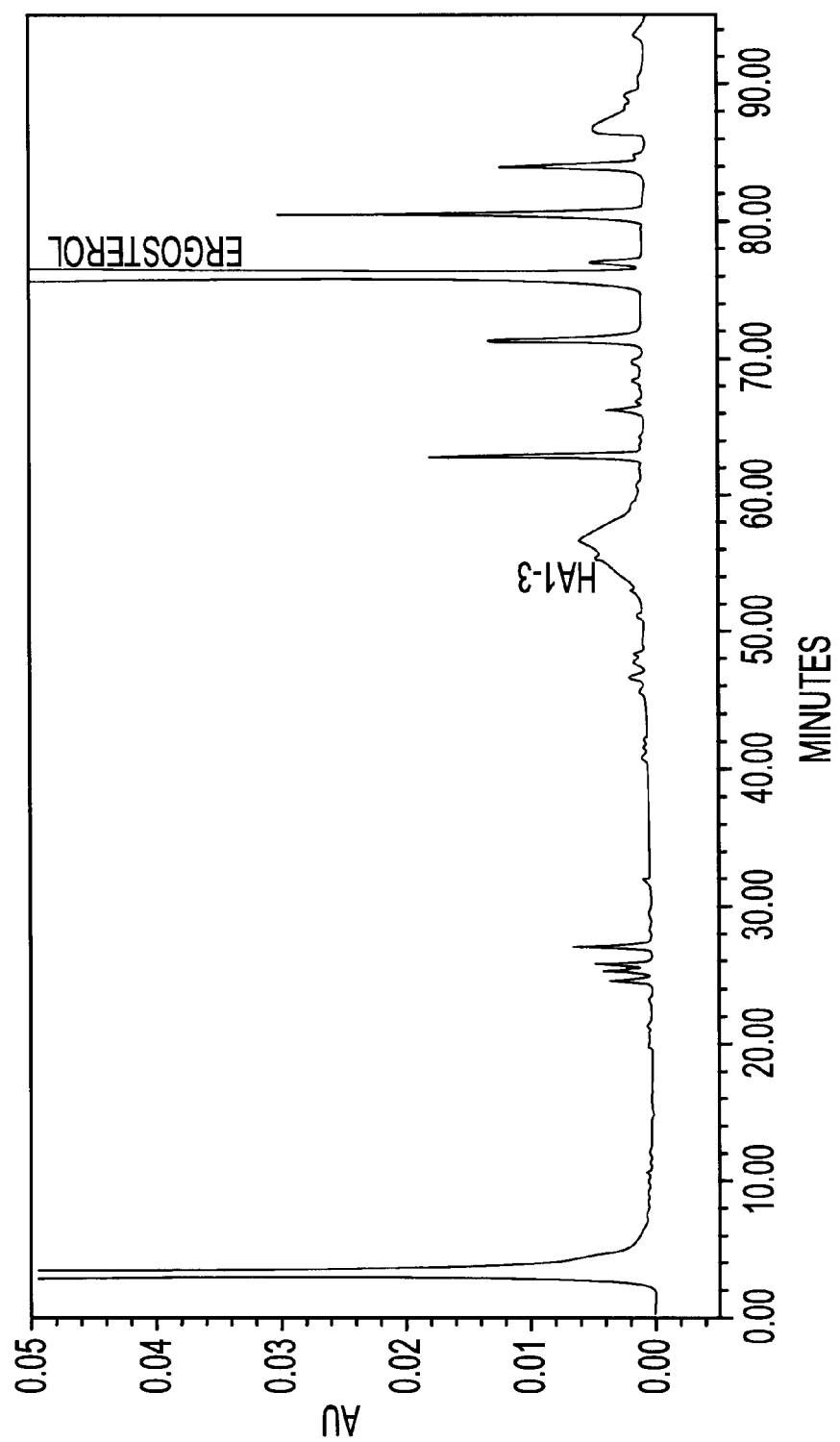
Figure 4B:
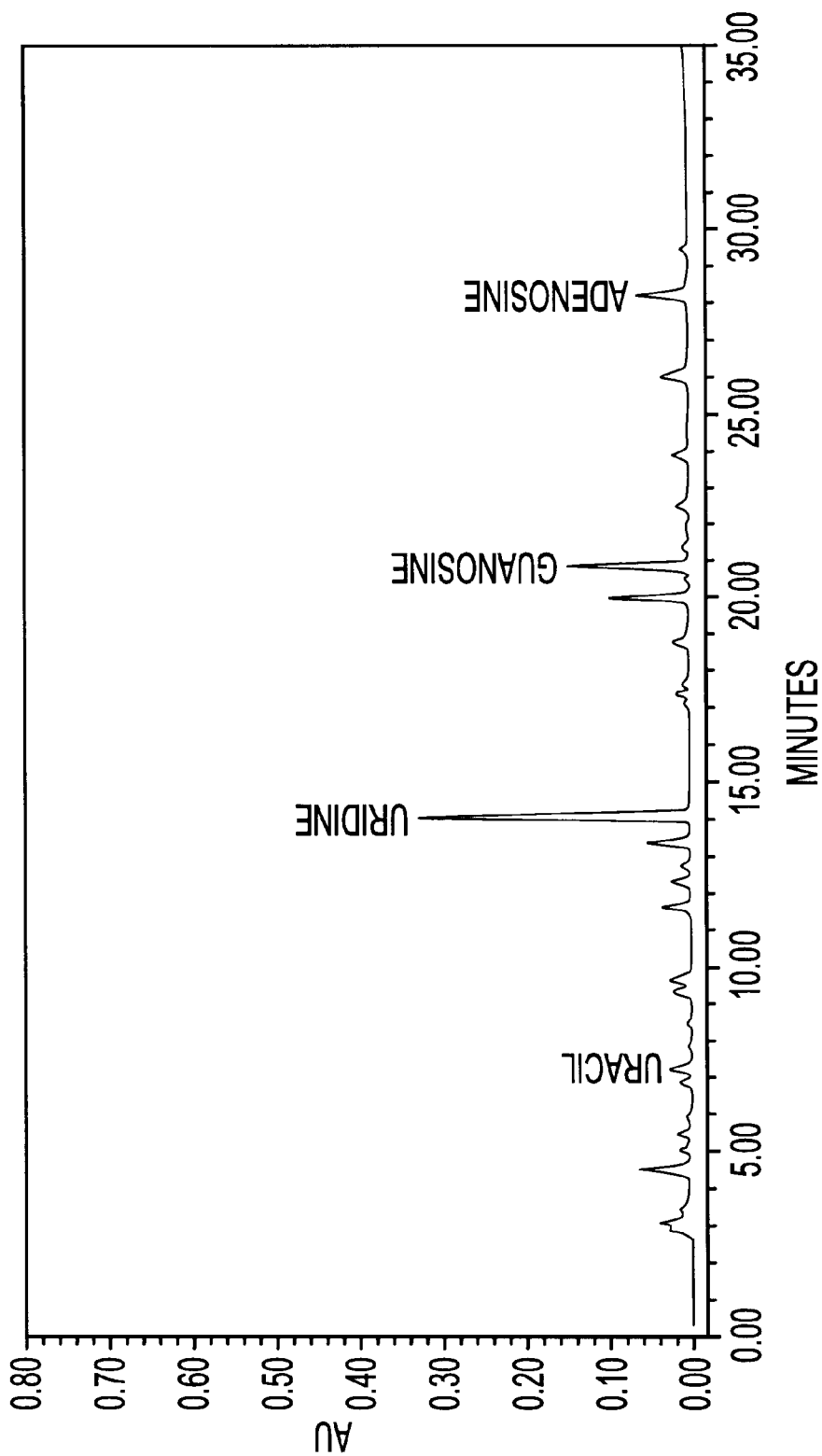

FIG. 4 shows HPLC analysis of H1A/ergosterol and nucleosides from wide type *Cordyceps sinensis*. H1A and ergosterol were separated and analyzed by RP-HPLC at 280 nm according to Lin U.S. Pat. No. 5,582,828. Nucleosides (i.e., uracil, uridine, guanosine, adenosine) were separated and analyzed by HPLC at 260 nm as described in Example 2 (infra). The chromatogram of H1A/ergosterol is shown in FIG. 4a. The chromatogram of nucleosides is shown in FIG. 4b.

V. DETAILED DESCRIPTION OF THE INVENTION

The solid state fermentation (SSF) of the present invention is useful for both large- and small-scale fungal productions. It is especially useful for production of H1A in *Cordyceps sinensis* as well as other metabolites in mushrooms such as *Trametes Versicolor, Antrodia Camphorata, Agaricus Blazei*, and *Ganoderma Lucidum*.

Fungal production using SSF is described in the flow chart of FIG. 1. FIG. 1 can be sub-divided into 3 columns. The left column shows how the mycelia of the fungus are selected and processed. This includes selection of wild, healthy mycelia by blade, or activation of fungal isolates from stock stored in liquid nitrogen. The selected mycelia are sterilized and placed into a plate or test tube containing solid culture media.

The middle column of FIG. 1 shows first how a solid culture medium is made and what the solid culture medium is. Examples of the solid culture medium include, but not limited to, PDA, YMA, and YEA, MEA, and PYG. The formulations of the solid state medium are provided in Table 1.

TABLE 1

FORMULATIONS OF SOLID CULTURE MEDIA

| | | |
|---|---|---|
| Potato Dextrose Agar (PDA) | Diced Potatoes | 300.00 g |
| | Glucose | 20.00 g |
| | Agar | 15.00 g |
| | Distilled Water | 1.00 L |
| Yeast Malt Agar (YMA) | Yeast Extract | 3.00 g |
| | Malt Extract | 3.00 g |
| | Peptone | 5.00 g |
| | Dextrose | 10.00 g |
| | Agar | 20.00 g |
| | Distilled water | 1.00 L |
| Yeast Extract Agar (YEA) | Yeast Extract | 5.00 g |
| | Glucose | 30.00 g |
| | Agar | 15.00 g |
| | Distilled Water | 1.00 L |
| Malt Extract Agar (MEA) | Malt Extract | 20.00 g |
| | Glucose | 20.00 g |
| | Peptone | 1.00 g |
| | Agar | 20.00 g |
| | Distilled Water | 1.00 L |
| Peptone Yeast Glucose Agar (PYG) | Peptone | 1.25 g |
| | Yeast Extract | 1.25 g |
| | Glucose | 3.00 g |
| | Agar | 20.00 g |
| | Distilled Water | 1.00 L |

The solid culture media are sterilized at 121° C. for fifteen minutes and poured into plates or test tubes (which in that case can form a slant culture) to cool down for use in mycelia multiplication. The mycelial growth is monitored by microscope and the mycelial colonies are documented by photography.

After proper mycelial growth, the cultured mycelia are transferred to a liquid medium in a 500 ml flask and incubated under rotating shaking conditions (e.g., at 240 rpm/min) for about 5–6 days. Examples of the liquid media include, but not limited to, PDB, YMB, and YEB, MEB, and PYGB. The cultured mycelia is then transferred to a 5000 ml shaker flask containing the hi same or different liquid culture medium and incubated under reciprocating shaking condition at 90 rmp/min for about 3–4 days. This is followed by aeration/agitation (Aeration: 1:0.3–0.5 ($O_2/CO_2$); Agitation: 200 rpm/min) and further incubation for 4–5 days. Again, the mycelial growth is monitored by microscope and documented by photography.

The right column of FIG. 1 shows the preparation of an SSF media, which includes the steps of: (a) heating and mixing the nutrients with a solid base material to boiling to form a solid base mixture, (b) letting the solid base mixture to cool down; and (c) adding calcium carbonate or gypsum (i.e., calcium sulfate dihydrate) to the solid base mixture to form the SSF medium. The SSF medium is granulated and packed into a bottle, which is then sterilized and placed in a cooling chamber for cooling.

The cultured mycelia from the 5000 ml shaker flask are transferred to the SSF bottle under laminar flow and operated in a sterile room. The SSF bottle containing the cultured mycelia is placed on the incubation shelves until harvest.

Appropriate temperature, humidity, and light are supplied in the culture room. After harvesting, the collected fungi are dried and ground into powder for further use. In addition, during the SSF incubation, fugal growth is continuously monitored by microscopy. The metabolites are measured by HPLC as described in Example 2 (infra).

As shown in FIG. 2b, Cordyceps sinensis is usually harvested at about 36–38 days of SSF incubation (most preferably at the 38th day of SSF incubation) because the production of H1A peaked at the $38^{th}$ days. However, the production of H1A does not coincide with the dried weight production of Cordyceps sinensis. As shown in FIG. 2a , the dried weight of Cordyceps sinensis starts to increase after 30 days of incubation in the SSF medium and plateau between 34 and 50 days. The results of FIG. 2 indicate that the harvest time should vary to accommodate the different purposes of the fungal production, i.e., if the purpose for propagating Cordyceps sinensis is to produce H1A, the SSF incubation period should be between 34–40 days, but for the purpose of producing sufficient Cordyceps sinensis dried weight, a prolonged SSF incubation period should be adequate.

The SSF media contain carbon source, nitrogen source, trace elements, vitamins, organic compounds, inorganic compounds, etc., which are particularly suitable for fungi growth. Depending on the requirements of individual fungus, pH and moisture can be adjusted and controlled accordingly.

The carbon source in the medium includes, but not limited to, any solid or liquid carbon source such as any starch-containing solution, glucose, mono-saccharide, polysaccharide, dextrin, various types of starch, maltose, saccharose, methyl cellulose, fructose, turanose, corn powder, etc.

The nitrogen source in the media includes, but not limited to, any solid or liquid nitrogen source such as defatted soybean powder, peptone, yeast paste, yeast syrup, peanut cake powder, yeast powder, wheat bran, casein or calcium caseinate, defatted beancake powder, etc. The weight ratio of the carbon source and the nitrogen source is preferably between 5:1 to 25:1. The amount of the nitrogen source in the SSF media is preferred to be maintained at an acceptable level or otherwise fugal growth and metabolite production would be greatly affected.

The kinds of vitamins which are useful for fungal growth include, but not limited to, Vitamin $B_1$, and Vitamin $B_2$ or nicotinic acid. The kinds of inorganic substances which are useful for fungal growth include, but not limited to, calcium sulfate, calcium carbonate, etc.

The proper pH for fungal growth is between 4.5 to 7.0. The proper amount of fungal inoculation is about 1–3% (w/v). The proper aeration is either natural air or an $O_2/CO_2$ ratio of 1:0.3–0.5 (v/v). The suitable temperature for fungal growth is between 17 to 27° C. (i.e., 22±5° C.). The water content in the SSF medium is 40–70%. The preferred light cycle is 30% light and 70% darkness. The relative humidity of the incubation chamber is 60–80%.

The following examples are illustrative, but not limiting the scope of the present invention. Reasonable variations, such as those occur to reasonable artisan, can be made herein without departing from the scope of the present invention.

EXAMPLE 1

Preparation of an SSF Medium

Table II shows an SSF medium which is suitable for Cordyceps sinensis propagation and production of H1A/ergosterol:

TABLE II

SSF MEDIUM FOR CORDYCEPS SINENSIS

| | Ingredients | Percentage in the Medium (wt %) |
|---|---|---|
| Composition A | Malt Extract | 2 |
| | Yeast Extract | 2 |
| | Peptone | 0.5 |
| | Glucose | 2 |
| | Water | 45.7 |
| Solid Base Composition B | Oatmeal | 45.7 |
| | Calcium Carbonate or Gypsum | 2 |

The SSF medium was prepared by mixing composition A with a solid base and heating the mixture to boiling so that water could be absorbed by the solid base. It was preferred that the water content in the solid base mixture was about 50%. The mixture was allowed to cool down. Calcium carbonate or gypsum was then added to the mixture. The final mixture was granulated to form the SSF medium granules. The granules were packaged into an SSF bottle which was sealed at the top. The SSF bottle was then autoclaved at 121° C., 1.5 kg pressure, for 1–2 hours, cooled down to room temperature, and placed in the incubation room under sterile condition.

EXAMPLE 2

HPLC Analysis of Fungal Metabolites

There were two groups of compounds which had been quantitatively and qualitatively detected by HPLC. The first group included H1A and ergosterol. The second group included nucleosides, i.e., uracil, uridine, guanosine, and adenosine.

H1A and ergosterol are polar/hydrophobic molecules. They could be effectively extracted by methanol (or other low-carbon alcohol), acetone, diethyl ether, ethyl acetate, chloroform, or methylene chloride. According to Lin et al., U.S. Pat. No. 5,582,828, the most desired solvents for H1A and ergosterol extraction were methanol and ethyl acetate. Nucleosides are water soluble compounds and mostly insoluble in alcohol. Therefore, to study the content of nucleosides, the dried fungal powder was dissolved in water, other than methanol or ethyl acetate.

Prior to the analysis H1A/ergosterol using HPLC, the methanol extract of Cordyceps sinensis was purified with a silica gel chromatography eluted with ethyl acetate/n-hexane (1:1, v/v). Six (6) fractions were collected from the silica gel column in which Fraction 2 was chosen for further HPLC analysis according to Lin et al., U.S. Pat. No. 5,582, 828.

For the analysis of nucleosides, no prior purification was added. Samples could be prepared from dissolving dried Cordyceps sinensis powder in water (1g of powder in 20 ml of $H_2O$). The extract was sonicated at room temperature for 15 minutes, and incubated at 40° C. water bath with 160 rpm for 20 minutes. The extract was then centrifuged at 3000 rpm for 5 minutes. The supernatant was collected, and passed through a 0.45 μm filter.

(1) RP-HPLC Analysis of H1A/Ergosterol

Reverse phase HPLC (RP-HPLC) (Cosmosil 5C18-AR, 4.6 I.D.×250 mm, 5 μm, Nacalai tesque) was used to purify and quantify H1A and ergosterol from Cordyceps sinensis sample. The column was eluted with a mixture of methanol and water (9:1, v/v) at a flow rate of 2.0 ml/min at room temperature. An ultraviolet detector was used with the wavelength set at 280 nm. The total retention time of the analysis was 90 minutes.

Figure 3A:
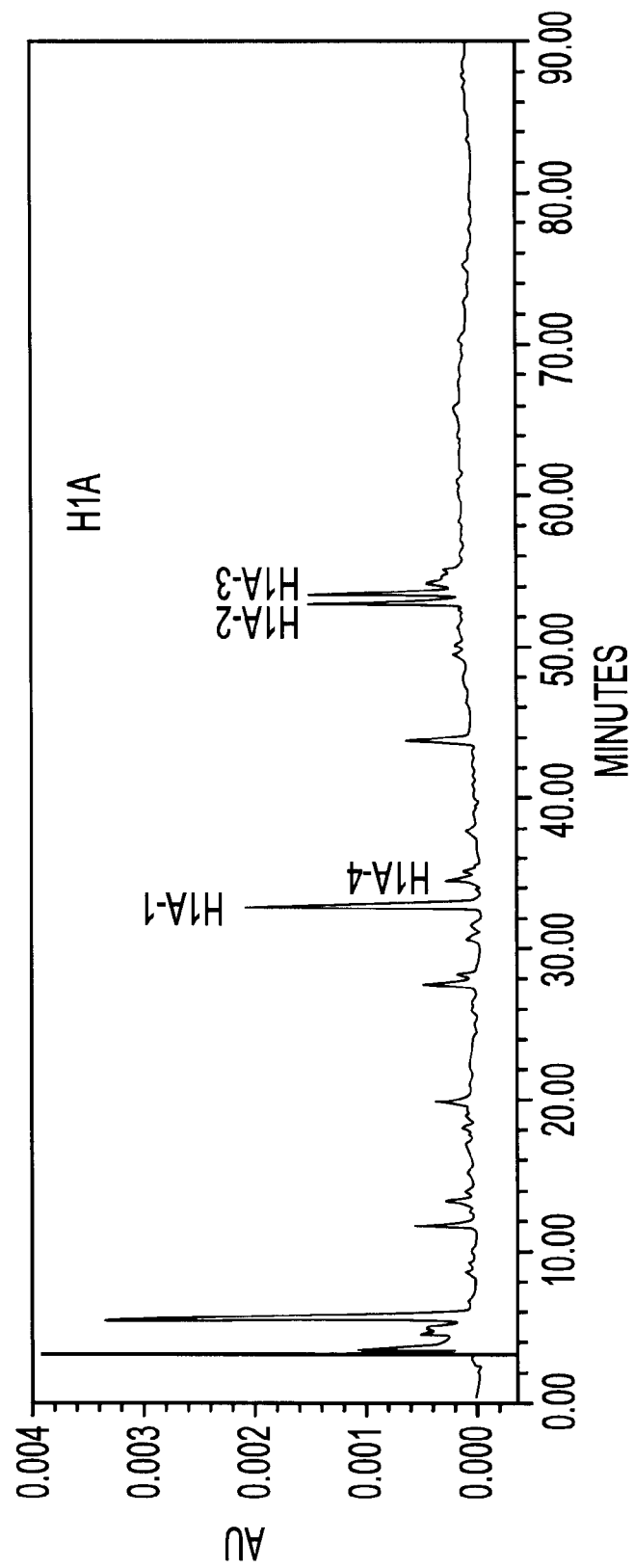
Figure 3B:
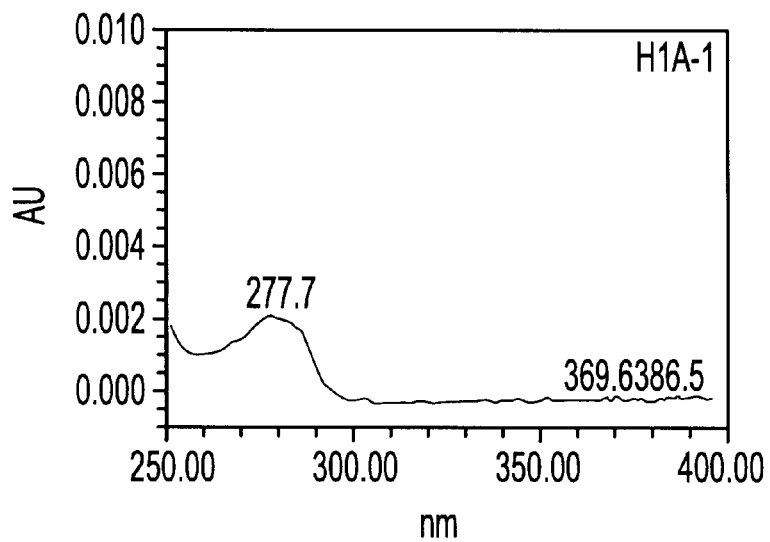
Figure 3C:
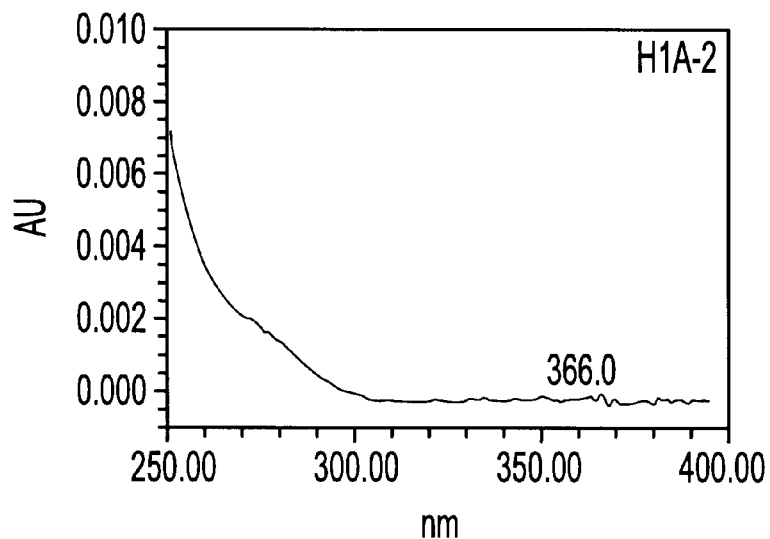
Figure 3D:
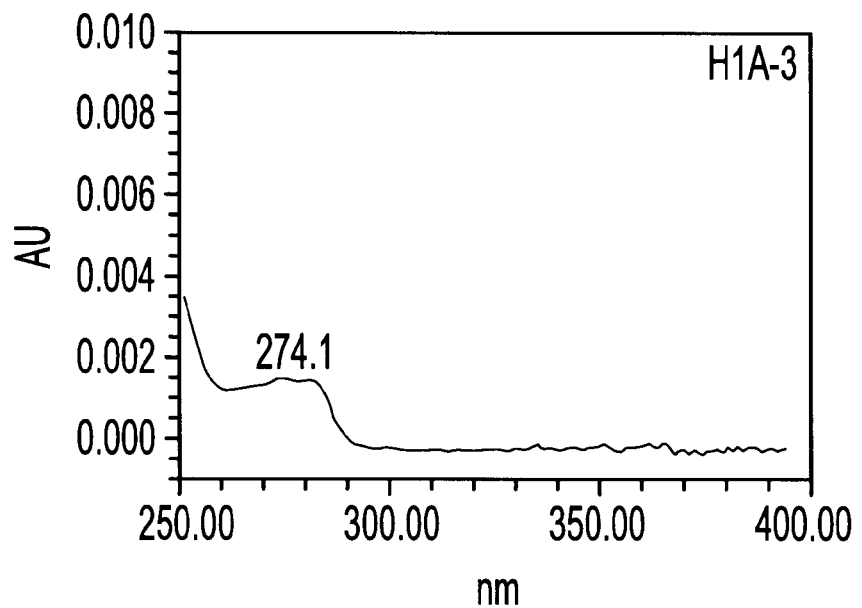

FIG. 3a is a HPLC chromatogram of a purified H1A sample. The chromatogram was detected at 280 nm. The H1A sample was a gift from Dr. Ching-Yuang Lin of U.S. Pat. No. 5,582,828. In U.S. Pat. No. 5,582,828, a similar RP-HPLC was described except that the detection was set at the wavelength of 254 nm. The chromatogram in FIG. 3a shows 4 separated peaks, namely, H1A-1, H1A-2, H1A-3, and H1A-4, denoting 4 possible sub-compounds of H1A. Alternatively, some of these sub-compounds could be contaminants of H1A. The retention time for H1A-1 was about 32.5 minutes, H1A-2 was about 52.5 minutes, H1A-3 was about 53.5 minutes, and H1A-4 was about 34 minutes. H1A-1, H1A-2, and H1A-3 were in significant amount. H1A-4 was in trace amount.

Figure 3E:
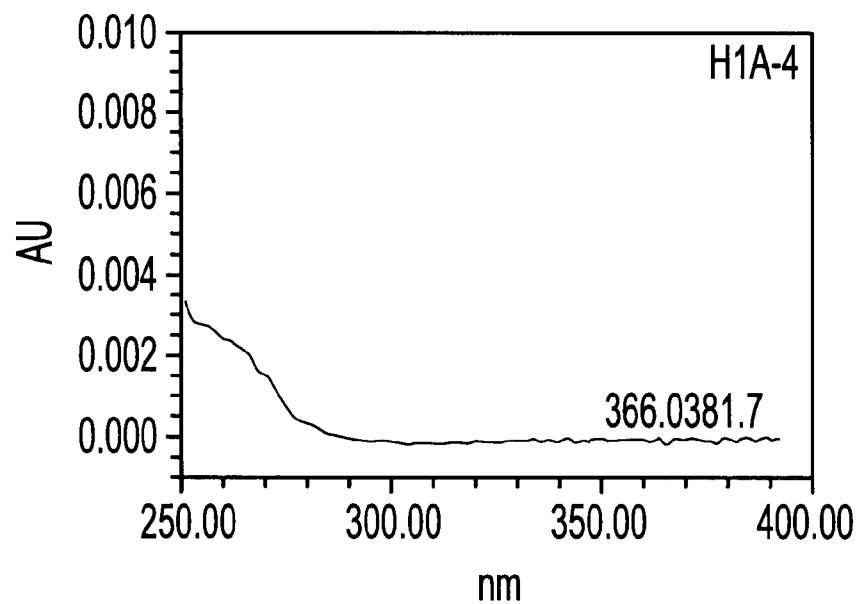

These four sub-compounds were further analyzed by scanning the spectrum at wavelength between 250 nm and 400 nm. FIGS. 3b–e show the spectra of H1A-1 (FIG. 3b), H1A-2 (FIG. 3c), H1A-3 (FIG. 3d), and H1A-4 (FIG. 3e). Only H1A-1 and H1A-3 show significant peak wavelength at 277.7 nm and 274.1 nm, respectively. The chemical structures and properties of these 4 sub-compounds remained to be determined.

FIG. 4a shows an HPLC chromatogram of H1A extracted from wild type *Cordyceps sinensis* C/2000-1 using the same RP-HPLC procedures as described in FIG. 3. *Cordyceps sinensis* C/2000-1 was the wild type *Cordyceps sinensis* which was directly purchased from herbs importer. The H1A-enriched sample was extracted from dried *Cordyceps sinensis* powder and extracted with methanol or ethyl acetate. The extract was further purified with silica gel chromatography. An aliquot of Fraction 2 of the silica gel elute was injected to the RP-HPLC column. The chromatogram of FIG. 4a shows an H1A-3 peak only, suggesting that H1A-1, H1A-2, and H1A-4 of FIGS. 3b–e might be contaminants of H1A. FIG. 4a also shows a significant peak of ergosterol with a retention time of 76 minutes.

(2) RP-HPLC Analysis of Nucleosides

RP-HPLC (RP-HPLC) using a precolumn Lichrospher RP-18 endcapped (5μm, 4.0 ID×10 mm, Merck), and a column (Cosmosil 5C18-AR, 4.6×250 mm, 5 μm) was used to purify and quantify nucleosides from *Cordyceps sinensis* sample. The column was eluted with a gradient containing (A) $H_2O$: $KH_2PO_4$: 10% $H_3PO_4$ (1000:2.72:1, v/w/v), (B) $CH_3CN$, (C) $H_2O$, and (D) $CH_3OH$ as described in Table III.

TABLE III

| | MOBILE PHASE GRADIENT FOR HPLC | | | | |
|---|---|---|---|---|---|
| Time (min.) | (A) | (B) | (C) | (D) | Curve |
| 0 | 100 | 0 | 0 | 0 | * |
| 25 | 60 | 0 | 20 | 20 | 6 |
| 30 | 20 | 0 | 20 | 60 | 6 |
| 35 | 100 | 0 | 0 | 0 | 6 |

The total retention time for the HPLC analysis of nucleoside was 35 minutes with a flow rate of 1.0 ml/min. The HPLC was run at 35° C. An ultraviolet detector was used with the wavelength set at 260 nm.

As shown in FIG. 4b, the retention time for uracil was about 7 minutes, uridine was about 14 minutes, guanosine was about 21 minutes, and adenosine was about 28 minutes.

EXAMPLE 3

Comparative Studies of H1A-3/Ertosterol/ nucleoside Production in *Cordyceps sinensis* Strain CS-36421 and VGH-TS-15

Productions of H1A-3 and ergosterol between *Cordyceps sinensis* strain CS-36421, which was cultivated by SSF, and strain VGF-TS-15, which was also cultivated by SSF, were analyzed by RP-HPLC. The method of analyzing H1A-3/ ergosterol was described in Example 2(1), supra.

The distributions of H1A-3 and ergosterol in *Cordyceps sinensis* strains CS-36421 and VGH-TS-15 were analyzed by first extracting the mycelia samples in ethyl acetate. Then, an equal amount of n-hexane (or petroleum ether) was added. The resultant mixture was filtered through glass wool before passing through a silica gel column. The silica gel column was continuously eluted with ethyl acetate/n-hexane (1:1, v/v). The eluents were sub-divided into 6 fractions and concentrated for HPLC analysis. Table III shows the detection of H1A-3 and ergosterol in *Cordyceps sinensis* strains CS-36421 and VGH-TS-15. Lot numbers 881601 and 881501 were from *Cordyceps sinensis* strain CS-36421, which was cultivated by the inventors of the present invention using SSF. Lot numbers 881526G, 8816065, 881608C, and 881703C were from *Cordyceps sinensis* strain VGH-TS-15, which was a gift from Dr. Ching-Yuang Lin of U.S. Pat. No. 5,582,828, and was cultivated using SSF:

TABLE III

| | RP-HPLC ANALYSIS OF *CORDYCEPS SINENSIS* FRACTIONS | | | | | | | | | | |
|---|---|---|---|---|---|---|---|---|---|---|---|
| | Fraction No. | | | | | | | | | | |
| Lot | Fr. 1 | | Fr. 2 | | Fr. 3 | | Fr. 4 | | Fr. 5 | | Fr. 6 | |
| number | H1A-3 | Ergosterol | H1A-3 | Ergosterol | H1A-3 | Ergosterol | H1A-3 | Ergosterol | H1A-3 | Ergosterol | H1A-3 | Ergosterol |
| *Cordyceps sinensis* CS-36421 | | | | | | | | | | | | |
| 881601 | − | − | + | + | − | + | − | − | − | − | − | − |
| 881501 | − | − | + | + | − | + | − | − | − | − | − | − |
| *Cordyceps sinensis* VGH-TS-15 | | | | | | | | | | | | |
| 881526G | − | − | + | + | − | + | | | | | | |
| 8816065 | + | + | + | + | − | + | | | | | | |

TABLE III-continued

RP-HPLC ANALYSIS OF *CORDYCEPS SINENSIS* FRACTIONS

| Lot number | Fr. 1 | | Fr. 2 | | Fr. 3 | | Fr. 4 | | Fr. 5 | | Fr. 6 | |
|---|---|---|---|---|---|---|---|---|---|---|---|---|
| | H1A-3 | Ergosterol | H1A-3 | Ergosterol | H1A-3 | Ergosterol | H1A-3 | Ergosterol | H1A-3 | Ergosterol | H1A-3 | Ergosterol |
| 881608C | − | − | + | + | − | + | − | − | − | − | − | − |
| 881703C | − | − | + | + | − | + | − | − | − | − | − | − |

+: *Cordyceps sinensis* strains containing H1A-3 and/or ergosterol.
−: *Cordyceps sinensis* strains not containing H1A-3 and/or ergosterol.

The results of Table III indicate that H1A-3 was primarily present in Fraction 2 of both CS-36421 and VGH-TS-15.

Table IV shows the percentages (%) of recovery and characteristics of Fractions 1–6 of the methanolic extract from *Cordyceps sinensis* strains 881501 and 881601. The percentage (%) of recovery was calculated as the amount of extract in each fraction divided by the amount of extract from the mycelial extract. Therefore, the total percentages of fractions 1–6 were not 100% due to losses during the isolation and purification steps.

TABLE IV

PERCENTAGES (%) OF RECOVERY AND CHARACTERISTICS OF EACH FRACTION OF *CORDYCEPS SINENSIS* METHANOLIC EXTRACT

| Fraction | | 1 | 2 | 3 | 4 | 5 | 6 |
|---|---|---|---|---|---|---|---|
| Yield(%) | 881501 | 0.030% | 1.47% | 0.030% | 0.58% | 0.58% | 0.65% |
| | 881601 | 0.013% | 0.73% | 0.011% | 0.65% | 0.21% | 0.37% |
| Characteristics | | Oily | Oily with solid precipitate | Thick oily | Gummy solid/paste-like | Gummy solid | Gummy solid |

The results of Table IV showed that Fraction 2 appeared to contain highest amount of polar materials, which could be an indication that fraction 2 contained the majority of H1A and/or ergosterol. The results of Table IV coincide with the findings in Table III. In addition, Table IV shows that Fraction 2 is characterized as being oily with solid substance precipitated, as opposed to Fraction 1 which was oily, or Fractions 3–6 which were more prone to thick oily/gummy solid.

Table V shows a comparative study of the nucleosides contents between *Cordyceps sinensis* strains CS-36421 and VGH-TS-15.

TABLE V

NUCLEOSIDE CONTENTS IN *CORDYCEPS SINENSIS* CS-36421 AND VGH-TS-15

| | Nucleoside Contents (mg) | | | | |
|---|---|---|---|---|---|
| Lot Number | Uracil | Uridine | Guanosine | Adenosine | Total |
| A. *Cordyceps sinensis* strain CS-36421 | | | | | |
| 881501 | 0.056 | 0.938 | 0.722 | 0.602 | 2.318 |
| 881601 | 0.060 | 0.752 | 0.640 | 0.510 | 1.962 |
| B. *Cordyceps sinensis* strain VGH-TS-15 | | | | | |
| 881526G | 0.128 | 0.042 | 0.050 | 0.042 | 0.262 |
| 8816126 | 0.162 | 0.015 | 0.024 | 0.019 | 0.220 |
| 881608C | 0.222 | 0.013 | 0.028 | 0.024 | 0.287 |
| 8816065 | 0.334 | 0.012 | 0.019 | 0.009 | 0.374 |
| 881701A | 0.407 | 0.016 | 0.024 | 0.015 | 0.462 |
| 881704D | 0.237 | 0.014 | 0.033 | 0.023 | 0.307 |

Two lot numbers of CS-36421 (i.e., 881501 and 881601) were analyzed for the nucleoside contents using RP-HPLC. The results are shown in Table VI(A). Six lot numbers of VGH-TS-15 (i.e., 881526G, 881612G, 881608C, 8816065, 881701A, and 881704D) were analyzed for the nucleoside contents using the same RP-HPLC method as those of CS-36421. The results are shown in Table VI(B). The nucleoside contents were calculated as mg of nucleoside per g of dried *Cordyceps sinensis*. The mg of nucleoside was measured by comparing the peak area of the nucleoside to that of the nucleoside standard.

The results of Table V show that the total nucleoside contents of CS-36421 were significantly higher than those of VG6H-TS-15, although individually, the uracil contents of CS-36421 were lower than those of VGH-TS-15.

The results of Table V are consistent with another experiment as shown in Table VI, which studied the amounts of ergosterol, adenosine, guanosine, uridine, and uracil in various lot numbers of CS-36421 and VGH-TS-15. Table VI(A) includes CS-36421 wild type, and Lots 1–4. Table VI(B) VGH-TS-15 Lot Nos. 881526G, 881612G, 881608C, 8816065, 881701A, and 881704D.

TABLE VI

COMPARISON OF ERGOSTEROL AND NUCLEOSIDES BETWEEN *CORDYCEPS SINENSIS* STRAIN CS-36421 AND VGH-TS-15

| Lot number | Substance content (mg/g) | | | | | |
|---|---|---|---|---|---|---|
| | Nucleosides | | | | | Steroids |
| | Uracil | Uridine | Guanosine | Adenosine | Total | Ergosterol |
| A. *Cordyceps sinensis* strain CS-36421 | | | | | | |
| Wild Type | 0.097 | 0.523 | 0.385 | 0.368 | 1.373 | |
| Lot 1 | 0.113 | 0.217 | 0.154 | 0.164 | 0.648 | 1.236 |
| Lot 2 | 0.110 | 0.415 | 0.284 | 0.267 | 1.076 | 1.519 |
| Lot 3 | 0.166 | 0.645 | 0.473 | 0.421 | 1.705 | 1.508 |
| Lot 4 | 0.245 | 0.593 | 0.443 | 0.407 | 1.688 | 1.974 |
| B. *Cordyceps sinensis* strain VGH-TS-15 | | | | | | |
| 881526G | 0.128 | 0.042 | 0.050 | 0.042 | 0.262 | 1.062 |
| 881612G | 0.162 | 0.015 | 0.024 | 0.019 | 0.220 | 0.700 |
| 881608C | 0.222 | 0.013 | 0.028 | 0.024 | 0.287 | 0.800 |
| 8816065 | 0.334 | 0.012 | 0.019 | 0.009 | 0.374 | 0.885 |
| 881701 A | 0.407 | 0.016 | 0.024 | 0.015 | 0.462 | 0.795 |
| 881704 D | 0.237 | 0.014 | 0.033 | 0.023 | 0.307 | 0.807 |

The results of Table VI show that except for the wide type of CS-36421 wherein ergosterol was not analyzed, CS-36421 Lots Nos. 1–4 contain much higher amounts of both total nucleosides and ergosterol.

EXAMPLE 4

Metabolites Analysis of *Ganoderma Lucidum*, *Antrodia Camphorata*, *Trametes versicolor*, and *Azaricus blazei*

Various fungi, which include *Ganoderma lucidum*, *Antrodia camphorata*, *Trametes versicolor*, and *Agaricus blazei*, were cultivated using SSF. Their metabolites were analyzed by HPLC. Table VII shows the amounts of triterpenoids, nucleosides, and ergosterol in *Ganoderma lucidum* and *Antrodia camphorata* after being cultivated in SFF.

TABLE VII

TRITERPENOID/NUCLEOSIDE/ERGOSTEROL CONTENTS IN *GANODERMA LUCIDUM* AND *ANTRODIA CAMPHORATA*

| Fungus Species | Triterpenoids | Substance content (mg/g) | | | | | Steroids |
|---|---|---|---|---|---|---|---|
| | | Nucleosides | | | | | |
| | | Uracil | Uridine | Guanosine | Adenosine | Total | Ergosterol |
| G. lucidum (A) | 2.448 | 0.154 | 0.313 | 0.257 | 0.301 | 1.025 | 0.561 |
| G. lucidum (B) | 1.355 | 0.125 | 0.249 | 0.172 | 0.199 | 0.745 | 0.532 |

TABLE VII-continued

TRITERPENOID/NUCLEOSIDE/ERGOSTEROL CONTENTS IN *GANODERMA LUCIDUM* AND *ANTRODIA CAMPHORATA*

| Fungus Species | Triterpenoids | Substance content (mg/g) | | | | | Steroids |
|---|---|---|---|---|---|---|---|
| | | Nucleosides | | | | | |
| | | Uracil | Uridine | Guanosine | Adenosine | Total | Ergosterol |
| A. camphorata (A) | 2.571 | 0.064 | 0.326 | 0.255 | 0.353 | 0.998 | 0.727 |
| A. camphorata (B) | 18.874 | 0.095 | 0.497 | 0.498 | 0.703 | 1.793 | 1.442 |

Table VIII shows the nucleosides content in *Trametes versicolor* after the fungus was cultivated in SSF. There are three different lots of Tramnetes versicolor, which are Lot Nos 1, 2, and 3.

TABLE VIII

NUCLEOSIDE CONTENT ANALYSIS OF *TRAMETES VERSICOLOR*

| Fungus Species | Substance Content (mg/g) | | | | |
|---|---|---|---|---|---|
| | Nucleosides | | | | |
| | Uracil | Uridine | Guanosine | Adenosine | Total |
| T. versicolor Lot 1 | 0.177 | 0.311 | 0.114 | 0.267 | 0.869 |
| T. versicolor Lot 2 | 0.246 | 0.212 | 0.103 | 0.241 | 0.802 |
| T. versicolor Lot 3 | 0.213 | 0.216 | 0.105 | 0.257 | 0.791 |

Table LX shows the nucleoside, ergosterol, and polysaccharide (%) contents in two different lots of *Agaricus blazei* (i.e., Lot Nos. 8851001W and 8851002CW). Noted that the uracil amount of *Agaricus blazei* was undetectable.

TABLE IX

NUCLEOSIDE/ERGOSTEROL/POLYSACCHARIDE CONTENTANALYSIS OF *AGARICUS BLAZEI*

| Fungus Species | Polysaccharide (%) | Substance content (mg/g) | | | | | Steroids |
|---|---|---|---|---|---|---|---|
| | | Nucleosides | | | | | |
| | | Uracil | Uridine | Guanosine | Adenosine | Total | Ergosterol |
| A blazei 8851001W | 9.26 | — | 0.157 | 0.105 | 0.211 | 0.473 | 0.416 |
| A. blazei 8851002 CW | 7.89 | — | 0.132 | 0.110 | 0.203 | 0.445 | 0.371 |

Having described the invention in detail and by reference to the preferred embodiments it will be apparent to those skilled in the art that modifications and variations are possible without departing from the scope of the invention as defined in the following appended claims.

We claim:

1. A method for propagating a fungus comprising:
   propagating mycelia of said fungus in a solid state fermentation culture using a solid state fermentation medium;
   wherein said fungus is one selected from the group consisting of *Trametes versicolor, Agaricus blazei, Ganoderma luciduni*, and *Antrodia camphorata*;

wherein said solid state fermentation medium comprises a carbon source (C), a nitrogen source (N), a vitamin and an inorganic substance; wherein said C: said N is at a ratio of about 5:1 to about 25:1 by weight; and wherein before propagating said mycelia of said fungus in said solid state fermentation medium, said mycelia are pre-cultivated first in a solid culture medium and then in a liquid culture medium.

2. The method according to claim 1, wherein said solid culture medium is one selected from the group consisting of potato dextrose agar, yeast extract agar, malt extract agar, yeast malt agar, and peptone yeast glucose agar.

3. The method according to claim 1, wherein said liquid culture medium is one selected from the group consisting of potato dextrose broth, yeast extract broth, malt extract broth, yeast malt broth, and peptone yeast glucose broth.

4. The method according to claim 1, wherein said carbon source is at least one selected from the group consisting of starch, glucose, monosaccharide, polysaccharide, dextrin, maltose, saccharose, methyl cellulose, fructose, turanose, and corn powder.

5. The method according to claim 1, wherein said nitrogen source is at least one selected from the group consisting of defatted soybean powder, peptone, yeast paste, yeast syrup, peanut cake powder, yeast powder, wheat bran, casein, calcium caseinate, and defatted beancake powder.

6. The method according to claim 1, wherein said vitamin is at least one selected from the group consisting of vitamin $B_1$, vitamin $B_6$, and nicotinic acid.

7. The method according to claim 1, wherein said inorganic substance is at least one selected from the group consisting of calcium sulfate and calcium carbonate.

8. The method according to claim 1, wherein pH of said solid state fermentation medium is between 4.5 and 7.0.

9. The method according to claim 1, wherein said solid state fermentation medium is maintained between 17° C. and 27° C.

10. The method according to claim 1, wherein said solid state fermentation medium has a water content of between 40 and 70%.

11. The method according to claim 1, wherein said solid state fermentation medium has a relative humidity of 60 and 80%.

12. The method according to claim 1, wherein said solid state fermentation medium is maintained at a light cycle of 30% light and 70% darkness.

13. The method according to claim 1, wherein said fungus is harvested after 20 to 60 days in said solid state fermentation medium.

14. The method according to claim 13, wherein said harvest time of said fungus is determined by analysis of a total nucleoside content of said fungus using high performance liquid chromatography (HPLC).

15. The method according to claim 13, wherein said harvest time of said fungus is determined by analysis of a total metabolites of said fungus using high performance liquid chromatography (HPLC).

16. The method according to claim 1, wherein said mycelia of said fungus in said solid state fermentation culture is transferred to another solid state fermentation culture for continuing cultivation of said fungus.

17. A method for propagating *Cordyceps sinensis* comprising:

propagating mycelia of *Cordyceps sinensis* in a solid state fermentation culture using a solid state fermentation medium;

wherein said solid state fermentation medium comprises a carbon source (C) and a nitrogen source (N) at a ratio of C:N about 5:1 to about 25:1 by weight; and wherein before propagating said mycelia of *Cordyceps sinensis* in said solid state fermentation medium, said mycelia are pre-cultivated first in a solid culture medium and then in a liquid culture medium.

18. The method according to claim 17, wherein said solid culture medium is one selected from the group consisting of potato dextrose agar, yeast extract agar, malt extract agar, yeast malt agar, and peptone yeast glucose agar.

19. The method according to claim 17, wherein said liquid culture medium is one selected from the group consisting of potato dextrose broth, yeast extract broth, malt extract broth, yeast malt broth, and peptone yeast glucose broth.

20. The method according to claim 17, wherein said solid state fermentation medium comprises malt extract, yeast extract, peptone, glucose, water, and a solid base.

21. The method according to claim 20, wherein said solid base is at least one selected from the group consisting of white rice, coarse rice, wheat, nude wheat, corn, barley, oat, and oatmeal.

22. The method according to claim 20, wherein said solid state fermentation medium further comprises calcium carbonate or gypsum.

23. The method according to claim 22, wherein said solid state fermentation medium comprises 0.3–4% by weight of malt extract, 0.3–4% by weight of yeast extract, 0.1–2% by weight of peptone, 1–5% by weight of glucose, 30–70% by weight of water, 40–60% by weight of solid base, and 0.3–4% by weight of calcium carbonate or gypsum.

24. The method according to claim 17, wherein said *Cordyceps sinensis* is harvested after 20 to 60 days in said solid state fermentation medium.

25. The method according to claim 24, wherein said harvest time of *Cordyceps sinensis* is determined by analysis of a total nucleoside content of said *Cordyceps sinensis* using high performance liquid chromatography (HPLC).

26. The method according to claim 24, wherein said harvest time of *Cordyceps sinensis* is determined by analysis of H1A content of said *Cordyceps sinensis* using high performance liquid chromatography (HPLC).

27. The method according to claim 24, wherein said harvest time of *Cordyceps sinensis* is determined by analysis of ergosterol content of said *Cordyceps sinensis* using high performance liquid chromatography (HPLC).

28. The method according to claim 17, said solid state fermentation medium further comprising a solid base;

wherein said solid base comprises at least one selected from the group consisting of white rice, coarse rice, wheat, nude wheat, corn, barley, oat, and oatmeal.

29. The method according to claim 17, said solid state fermentation medium further comprising a solid base which is oatmeal.

30. The method according to claim 20, wherein said solid base is oatmeal.

* * * * *